United States Patent [19]

Drost

[11] 4,227,407
[45] Oct. 14, 1980

[54] VOLUME FLOW MEASUREMENT SYSTEM

[75] Inventor: Cornelis J. Drost, Ithaca, N.Y.

[73] Assignee: Cornell Research Foundation, Inc., Ithaca, N.Y.

[21] Appl. No.: 965,456

[22] Filed: Nov. 30, 1978

[51] Int. Cl.³ .............................................. G01F 1/66
[52] U.S. Cl. .................................. 73/194 A; 128/663
[58] Field of Search ...................... 73/194 A; 128/663

[56] References Cited

U.S. PATENT DOCUMENTS

| | | | |
|---|---|---|---|
| 2,746,291 | 5/1956 | Swengel | 73/194 A |
| 3,817,098 | 6/1974 | Brown | 73/19 A |
| 3,906,791 | 9/1975 | Lynnworth | 73/194 A |
| 4,011,753 | 3/1977 | Hausler | 73/194 A |

OTHER PUBLICATIONS

R. D. Rader "A Diameter-Independent Blood Flow Measurement Technique" *Medical Instrumentation*-vol. 10, No. 4., pp. 185-188, Jul.-Aug., 1976.

*Primary Examiner*—Charles A. Ruehl
*Attorney, Agent, or Firm*—Jones, Tullar & Cooper

[57] ABSTRACT

An apparatus and method for direct measurement of the volume flow of fluids through a tube, using an interferometric transit time technique is disclosed. First and second transducers for producing and receiving waves which are capable of being modified by the flow of the fluid in the conduit are positioned so that the conduit is fully and evenly illuminated by the waves. The transducers are located with respect to the conduit so that there will be a component of fluid flow along the axis of the illuminating wave beam. Means are provided to first activate one transducer to transmit waves while the other is in a receive mode and thereafter to place the second transducer in a transmit mode while the first is switched to its receive mode. The received waves are converted to corresponding electric signals by the corresponding transducers, and these signals are periodically sampled and stored for comparison. The result of this comparison is an electric signal which is proportional to fluid flow and is to a high degree independent of flow profile, conduit geometry, and alignment of the conduit within the probe. The device is particularly useful in measuring the flow of blood through a vessel.

13 Claims, 6 Drawing Figures

VOLUME FLOW MEASUREMENT SYSTEM

BACKGROUND OF THE INVENTION

The invention described herein was made in the course of work under a grant award No. HL 19019 from the Department of Health, Education, and Welfare.

The present invention relates, in general, to the measurement of the volume flow of fluids through conduits, and more particularly to the measurement of the flow of blood through arteries and veins.

The technique of utilizing wave signals such as light or sound for measuring the velocity of flow of a fluid which is transparent to the wave is well known. For example, the use of light in such measurements was established in a fundamental physical experiment in 1851, where two coherent light beams were simultaneously projected upstream and downstream of a flowing liquid. A light interference pattern was produced, with the position of maxima and minima reflecting the velocity of the flowing medium. More recently, acoustic waves in the ultrasonic frequency range have been used to measure the flow velocity of liquids and gases that are acoustically transparent. In this type of measurement, a transmitter and a receiver, which may be transducers constructed from a piezoelectric material, are positioned in such a way that the transit time of the sound wave between the transmitter and the receiver is affected by a component of the flow of the medium being measured. The transit time of a sound wave traveling between the two transducers is a function of the relative average velocity of the second conductive medium times the acoustic path length. If it is desired to obtain the average velocity from this transit time measurement, the distance over which the velocity is averaged must be measured.

The method of using acoustic waves for measuring the flow velocity in liquids and gases has been implemented for biomedical use, with intravascular systems being provided to utilize the difference in transit time between an upstream and a downstream projected burst of sound to measure flow velocity with a known zero reference, and a similar scheme has been used for an extra-vascular flow measurement device. However, because it is necessary to obtain a measurement of the path length followed by the waves in transversing the conduit carrying the fluid to be measured in order to deduct average velocity, such devices have presented problems not only in general measurement applications, but particularly in the measurement of blood flow, for it is often extremely difficult to obtain an accurate measurement of the inside diameter of a conduit such as, for example, a blood vessel. Further, if it is desired to obtain volume flow data, it is necessary to know with great accuracy both the vessel geometry and the relationship between sample average velocity and total average velocity, which is a function of the flow profile across the diameter of the conduit, and again, such data is usually very difficult to obtain, particularly in blood vessel measurements. Any error in this dimension produces a proportional error in the volume flow measurement.

Another source of error in prior ultrasonic flow measuring devices is the fact that the sound waves produced by one transducer may be reflected by the vessel walls and produce false signals in the receiving transducer. Where the medium to be measured is flowing through an accessible conduit which has easily measurable dimensions, many of these problems can be avoided, but where the flow is through a flexible conduit of uncertain internal diameter, such as a blood vessel, additional errors have been produced in prior systems. But even where the conduit is accessible, minor variations in size can produce errors, as can misalignment of the conduit with respect to the transducers. The numerous sources of error have made prior measurements of fluid flow volume inaccurate and unreliable.

SUMMARY OF THE INVENTION

It is, therefore, an object of the present invention to provide a system for directly measuring the volume of flow through a conduit such as a blood vessel.

It is a further object of the invention to provide a probe for use in measuring blood flow through a vessel, wherein the probe can be applied nonconstrictively around the vessel to reduce the impact of such measurement on the patient.

It is further an object of the invention to provide a method and apparatus for obtaining an electric signal which is proportional to volume flow and which is to a high degree independent of the profile of the flow within the vessel carrying the medium of interest, is independent of vessel geometry, including vessel size and wall thickness, and which is independent of the alignment of the vessel within the probe.

Briefly, the present invention is directed to a method of, and apparatus for, directly measuring the volume flow of a fluid medium. In accordance with the invention, such a measurement may be made by means of a transit time flow meter if the transmitter and the receiver are so constructed that the full cross-sectional area of the flow affects, with even sensitivity, the wave travelling through the fluid medium. In a preferred form, the present invention comprises a probe having first and second spaced transducers for producing and for receiving waves, such as acoustic waves, which are capable of being modified by the flow of the fluid medium, or stream, the volume flow of which is to be determined. The transducers may be located on opposite sides of the conduit, or vessel, through which the fluid passes, although in a preferred embodiment they may be on the same side of the vessel with a reflective surface being provided on the opposite side of the conduit to define a reflective path from one transducer through the conduit to the reflective surface and then back through the conduit to the second transducer. The transducers provide an essentially uniform wave field of sufficient dimension to insure uniform illumination of the entire diameter of the vessel.

Electrical circuitry is provided to supply an energizing signal first to one transducer and then to the other so that acoustic wave beams traveling first in one direction and then in the opposite direction between the transducers are generated. When one transducer is transmitting, the other is in a received mode, and vice versa. The received signals from both transducers are fed alternately to a suitable receiver circuit and thence to a synchronous detector which multiplies the received signal with the original energizing signal. The output of the synchronous detector is a direct current signal which is proportional to the time delay between the two compared signals, and this output is integrated to produce a signal which is proportional to the average reading for this time delay.

The transducers are so located with respect to the flow conduit that the fluid stream in the conduit will have a component of flow along the axis of the acoustic wave beam between the transducers so that the flowing medium will affect the transit time of the acoustic wave. Accordingly, the transit time of the acoustic wave traveling from one transducer to the other will be reduced by a downstream component of flow, while the reverse beam will travel more slowly due to an upstream component, and its transit time will be increased. The upstream and downstream components thus alternate, and produce alternate direct current output signals from the synchronous detector and thus from the integrating circuit, which signals are stored in corresponding upstream and downstream sample and hold circuits. The information in the sample and hold circuits is updated for each measurement cycle, and the values contained in the two circuits are subtracted to produce a resultant output signal which is proportional to the volume flow in the conduit. The sequence of measurements is repeated every millisecond to produce a continuous reading of the flow. This measurement value is substantially independent of the profile of the flow within the conduit, the conduit geometry, and in a preferred embodiment of the probe, of the alignment of the conduit within the wave field defined by the transducers. The transducers may be mounted in a suitable housing for use as a volume flow probe which overcomes the disadvantages of prior art probes.

BRIEF DESCRIPTION OF THE DRAWINGS

The foregoing and additional objects, features and advantages of the present invention will become apparent to those of skill in the art from a consideration of the following detailed explanation of a preferred embodiment of the invention, taken in conjunction with the accompanying drawings, in which.

DESCRIPTION OF PREFERRED EMBODIMENTS

Figure 1:
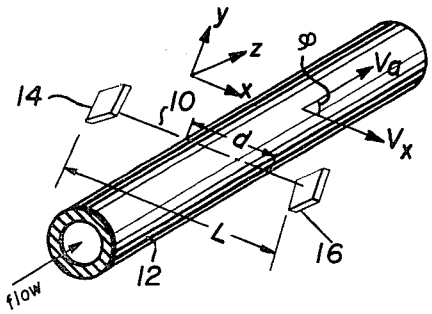
FIG. 1 is a diagrammatic illustration of the geometry of a small wave beam intersecting a conduit carrying a fluid to be measured in a transit time flowmeter.

In FIG. 1 there is illustrated in diagrammatic form the geometry of a small wave beam 10 intersecting a conduit or similar vessel 12 which carries a moving fluid to be measured. The conduit 12 may be of any geometric shape in cross-sectional and, for example, may be a blood vessel such as a vein or artery, and the fluid may be blood. The wave beam 10 passes between a pair of transducers 14 and 16 which lie on opposite sides of the conduit 12 and which, when activated by a suitable electric signal, will generate beam 10. The transducers may be piezoelectric devices of the reciprocal type; that is, of the type activated by suitable electrical signals to produce an acoustic wave beam, with the activated transducer serving as a transmitter and the opposite transducer serving as a receiver. As indicated in FIG. 1, the emitted beam travels along an axis X which is perpendicular to the y-z plane of the transducer and is directed to intersect the axis of flow $V_a$ at an angle $\phi$ so that there is a component of flow $V_x$ along the axis of the beam.

The transit time of the acoustic wave beam between the two transducers is proportional to the distance d, which is the length of the beam path in the vessel 12 and which is dependent upon the dimensions of the vessel, multiplied by the average velocity of the fluid encountered during the passage through distance d. The velocity of the fluid flow changes the apparent velocity of sound along the path 10, and the transit time therefore reflects the velocity of the moving medium. A beam of small lateral dimensions, as compared to the diameter of the vessel, will sample the flow passage through its intersection with the vessel so that the transit time will reflect the average fluid velocity encountered along the path length of the beam within the vessel.

Figure 2:
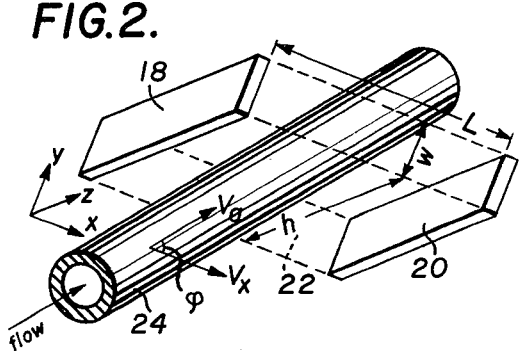
FIG. 2 is a diagrammatic illustration of a constant intensity, full conduit illumination produced with a rectangular wave beam passing between two transducers spaced on opposite sides of the conduit, in accordance with the present invention.

In accordance with the present invention, volume flow information can be obtained by illuminating the entire cross section of the vessel 12 with a constant level of wave energy. This is illustrated in FIG. 2, wherein the transducers of FIG. 1 are replaced by laterally extended upstream and downstream transducers 18 and 20 which have a sufficiently large lateral dimension to produce a rectangular beam 22 which encompasses the full diameter of conduit 24. The transducers may be rectangular pieces of LTZ-2 piezoelectric ceramic, produced by Transducer Products, Torrington, Conn., operated in a thickness mode and lucite backed, with no impedance matching and with a nominal resonance frequency of 2 MHz. To produce acoustic wave signals at ultrasonic frequencies, the transducers are sufficiently wide to insure that the beam 22 will encompass the largest diameter vessel that is to be measured, and in one form of the invention, the transducers were 4 mm in width (w) along the y axis of FIG. 2 and 11.6 mm in height (h) along the z axis. In one embodiment of the invention, the two transducers 18 and 20 were aligned with each other for maximum acoustic signal transfer at a distance of about 25 mm. It was found that the cross-coupled acoustic field produced by this arrangement of transducers was uniform across the central 70 percent of the height h of the transducer when operated at or near a frequency of 2.15 MHz.

As indicated diagrammatically in FIG. 1, the vessel carrying the fluid flow to be measured is interposed between the transducers and within the field of beam 22 in such a way as to insure that there is a component of fluid flow along the direction of the beam. The area between the transducers not occupied by vessel 24 is filled with an acoustically transparent material. This material will depend upon the nature of the measurement being made, but in a typical use for the measurement device of the present invention, where blood flow in a blood vessel is being measured, this space may be occupied by water, scar tissue or the like.

By insuring that the entire cross section of the vessel 25 is illuminated by an acoustic wave beam of constant intensity, every infinitesimal constituent of the beam which passes through vessel 24 acquires a transit time deviation which is proportional to its path length through the flowing medium, multiplied by the average fluid velocity during that passage. All of these beam constituents are received and summed on the face of the receiving transducer to produce a signal which has an overall phase deviation proportional to the volume flow. Those parts of the acoustic beam which do not pass through the vessel do not contribute to the transit time deviation and thus do not affect the output signal. Since this is the case, it is not necessary to provide a constructive fit between the transducers and the vessel, and any size vessel can be measured as long as it has a dimension smaller than the dimension of the uniform portion of the acoustic wave beam.

Although the measuring system of the present invention is shown in FIG. 2 without a surrounding housing supporting the transducers, it will be understood that such a housing would normally be provided, preferably in the form of a suitable probe which would permit easy handling of the unit by the operator, which would maintain the proper spatial relationship between the transducers, and which would provide a suitable access opening for reception of the fluid-carrying vessels to be measured. Such a probe housing may take any desired form, and the specifics of its construction are not a part of the present invention.

Figure 3:
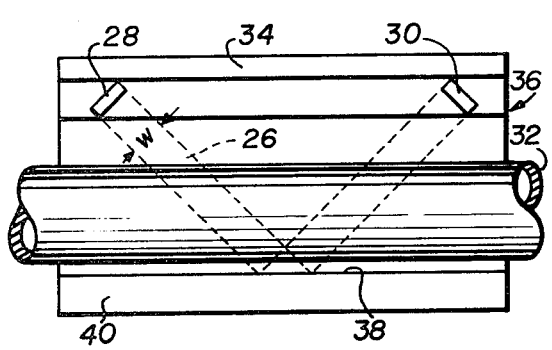
FIG. 3 is a side view of a probe carrying a pair of wave beam transducers located on the same side of the vessel carrying the fluid to be measured, in accordance with a modified version of the present invention.
Figure 4:
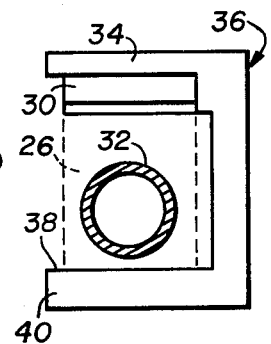
FIG. 4 is an end view of the probe of FIG. 3.

It has been found that the flow-related output obtained from transducers 18 and 20 is not only dependent upon the flow velocity within the vessel, but is also dependent upon the angle between the measuring beam 22 and the axis of vessel 24. Accordingly, the output is sensitive to vessel misalignment and to flow disturbances within the vessel such as secondary and meandering flow. However, this problem may be solved by the preferred embodiment of the invention illustrated in FIG. 3, wherein a sound beam 27 projected by either one of two transducers 28 and 30 twice intersects the vessel 32 carrying the fluid to be measured. As shown in FIGS. 3 and 4, the transducers 28 and 30 are suitably mounted to an upper leg portion 34 of a probe generally indicated at 36. The transducers are mounted at angles with each other and with the vessels 32, but on the same side of the vessel so that the beam projected by one transducer passes a first time through the vessel, is reflected from the upper surface 38 of an oppositely disposed leg 40 of the probe housing and passes a second time through the vessel for return to the second transducer. This reflective path produces counteracting angle deviations at the two passages, and overcomes the measurement problems created by vessel misalignment and by flow disturbances. The electric signals at the receiving transducer resulting from the sound beam passages include terms which represent counteracting effects from each of the two passages through the vessel, and these counteracting effects cancel each other in the resultant output. Accordingly, the arrangement of FIGS. 3 and 4 provides a flowmeter which is substantially insensitive to misalignment of the flow path within the beam field. It will be noted that the reflective surface 38 should be of a solid material such as stainless steel to insure proper contact between the two transducers.

Figure 5:
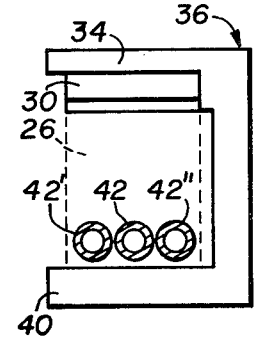
FIG. 5 is an end view of the probe of FIG. 3, showing the measurement of conduits of relatively small size.

As long as a homogenous beam field is provided across the height (h) of the transducers, the volume flow measurement will be unaffected by the particular size or location of the fluid-carrying vessel within the field. Accordingly, as illustrated in FIG. 5, a relatively small fluid-carrying vessel such as that indicated at 42 may be centrally located in the beam or may be moved to either the left or right hand sides of the beam, as indicated at 42′ or 42″, without affecting the accuracy of the measurement. Similarly, a larger vessel such as that indicated at 32 in FIG. 4 may be positioned anywhere within the beam, or a vessel having a diameter equal to the height of the beam may be inserted in the probe housing, all without appreciably affecting the accuracy of the volume flow reading. It will be understood that if the beam is not uniform along the entire height of a given transducer, then the vessel or vessels will be positioned in the housing within the uniform portion of the beam produced thereby; In the interest of clarity, therefore, it will be hereinafter assumed that the dimension "h" of the transducers refers to the uniform beam field portion of the transducers.

It has been found that the present invention permits measurement, with a high degree of accuracy, of a wide variety of flow rates through conduits having any diameter that will fall within the uniform acoustic field produced by the transducers. It has further been found that such measurements are not affected by turbulence in the fluid flow.

The walls of the conduit through which the fluid flows in the flowmeter of the present invention should be of a material that does not induce in the acoustic beam an attenuation differing from the fluid and the surrounding medium, for if the conduit has such an effect, it would distrub the balance between the various portions of the cross-coupled acoustic signal. At the frequency employed in the aforementioned example (e.g., 2.15 MHz), satisfactory results have been obtained with unstretched, thin-walled latex tubing as well as with blood vessels.

Figure 6:
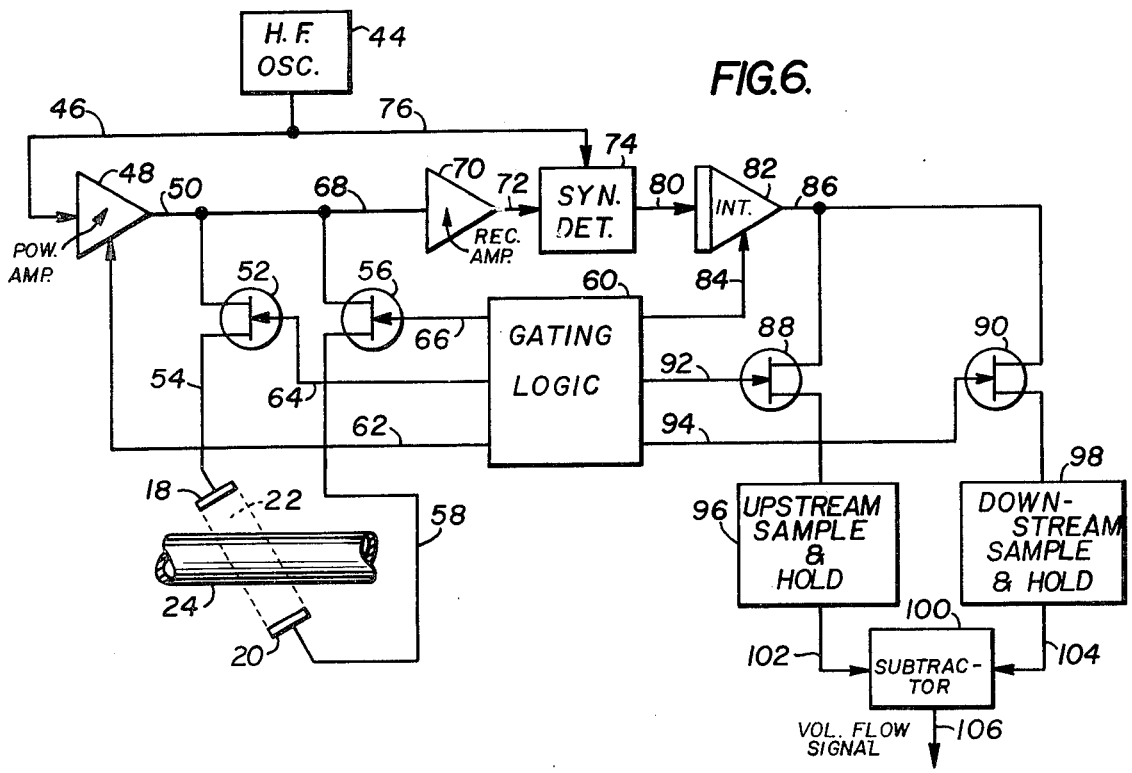
FIG. 6 is a block diagram of the transit time flowmeter circuitry of the present invention.

Suitable circuity for operating the volume flowmeter illustrated in FIGS. 2 and 3 is set out in block diagram form in FIG. 6 and is shown as being connected to transducers 18 and 20 spaced on opposite sides of a flow conduit 24 in the arrangement set forth in FIG. 2. It should be understood, however, that the same circuitry may be used for the transducer configuration of FIG. 3. The flowmeter circuit includes a high frequency oscillator 44 which generates a continuous electrical signal at an amplitude and frequency sufficient to activate one or the other of transducers 18 and 20 to cause them to produce ultrasonic acoustic waves of the desired frequency.

The high frequency oscillator 44 is connected by way of lead 46 to the input of a gated power amplifier 48 which, when gated on, produces an amplified high frequency drive signal on its output line 50. The drive signal is supplied to a semiconductor gate 52, which may be a field effect transistor, and when the gate is conductive, the drive signal is fed through lead 54 to the upstream transducer 18. The drive signal on line 50 is also supplied to a second semiconductor gate 56 and, when it is conductive, through its output lead 58 to the downstream transducer 20 to provide a driving signal thereto. A gating logic circuit 60, which may be a conventional counter driven by a suitable clock, produces gating signals selectively on output lines 62, 64, and 66 to control the operation of gated power amplifier 48, gate 52, and gate 56, respectively, thereby to control the flow of high frequency drive signals from the oscillator 44 to the transducer 18 or 20. During the time that drive signals flow to one or the other of the transducers, the circuit is in what may be termed a "transmit" mode.

Transducers 18 and 20 are also connected through their respective gating semiconductors 52 and 56 to input line 68 of a receiver amplifier 70, whereby acoustic signals received by the transducers and converted to corresponding audio frequency electrical signals may be supplied by way of their corresponding gating semiconductors to the receiver amplifer. To permit reception of acoustic signals, the gating logic provides a "receive" mode in which outputs on lines 62, 64 and 66 must be activated to turn off power amplifier 48 and to cause gate 52 or 56 to become conductive, depending on which transducer is receiving signals. The received signals are fed to and amplified in receiver amplifier 70 and then are fed by way of line 72 to one input of a synchronous detector 74 which has, as its second input, the output from high frequency oscillator 44. This oscillator signal is carried by way of line 76 to the detector, which multiplies the received signal from one or the other of transducers 18 and 20 with the output from the oscillator. In this specific arrangement the synchronous detector, which may be balanced demodulator such as Motorola Type MC1496, is overbiased on both of its inputs to produce a variable DC output signal on line 80 which is instantaneously proportional to the time difference in the zero crossings of the two input signals on lines 72 and 76. This DC signal is, therefore a function of the time delay imposed on the transmitted acoustic wave by moving fluid in the vessel being measured. The DC signal is applied to the input of a gated integrate and hold module 82 which is controlled from the gating logic circuit 60 by way of line 84 so that the integrator is normally "reset", but is on during the reception of acoustic wave signals. During this on period, the varying DC signal on line 80 is integrated to produce a signal on output line 86 from the integrator which is proportional to the average reading during that period, and thus is proportional to the time delay imposed on the acoustic signal.

The average time delay signal obtained at the output of integrator 82 is supplied to a pair of sample control gates 88 and 90. Preferably, these are semiconductor gates such as field effect transistors which are selectively activated for short periods; e.g., 10 micro seconds, by output signals on lines 92 and 94, respectively, from the gating logic circuit 60. Thus, for example, gate 88 may be activated after an acoustic wave generated by the "upstream" transducer 18 and received on transducer 20 has been averaged in integrator 82; similarly, the gate 90 may be activated after the "downstream" acoustic signal has been received by transducer 18 and averaged in the integrator. Activation of gates 52 or 56, the integrator 82, and one or the other of gates 88 and 90 may be termed a "receive" mode for the circuit.

When gate 88 is conductive, the output from the integrator is fed to an upstream sample and hold circuit 96 for storage and subsequent comparison with the downstream sample which is fed to the downstream sample and hold circuit 98 from the integrator when gate 90 is conductive. The DC voltages stored on the two sample and hold modules may be comparied in a subtractor 100 connected to modules 96 and 98 by way of lines 102 and 104, respectively, with the output of the subtractor being a resultant signal on output line 106 which is proportional to the volume flow intersecting the acoustic beam 22.

To accomplish the desired measurement of volume fluid flow, the circuit is operated in two cycles, each of which includes a transmit mode and a receive mode. In the first, or upstream, cycle transmit mode, power amplifier 48 and gate 52 are on so that transducer 18 transmits acoustic signals, while the receive gate 56, integrator 82 and sample control gates 88 and 90 are off. In the first cycle receive mode, amplifier 48 and gate 52 are off, gate 56 is conductive, integrator 82 is turned on for a fixed period, and gate 88 is subsequently made conductive, to permit storage of the averaged output from the integrator in sample and hold circuit 96. The second, or downstream, cycle is similar to the first, but with the roles of transducers 18 and 19 reversed. Thus, in the second cycle transmit mode, amplifier 48 and gate 56 are on, while gate 52, integrator 82 and gates 88 and 90 are off, so that transducer 20 can transmit an acoustic wave. Thereafter, in the second cycle receive mode, amplifier 48 and gate 56 are turned off, gate 52 becomes conductive, and integrator 82 and gate 90 are operated to permit storage of received wave signals in the downstream sample and hold circuit 98.

The logic circuit 60 controls the operation of the system by switching it from one cycle and mode to the next. In a preferred operation of the system, the transmitting transducers are connected to amplifier 48 to cause the transducer to emit a burst of acoustic wave signals for a period of time which is less than the time required for the acoustic waves to travel the distance to the receiving transducer. In the present embodiment, a burst 10 $\mu$sec in duration was found to be satisfactory, with the transmitted burst of acoustic wave signals arriving at the receiving transducer after a delay of approximately 16 $\mu$sec.

At the completion of each transmit and receive mode, the logic circuit holds all of the gate components off for a preselected period (for example, 500 $\mu$sec) to permit all of the echos produced by the emitted acoustic wave bursts to die out; thereafter a next measurement is taken.

After the circuit has completed its upstream and downstream cycles, the sample and hold modules 96 and 98 contain DC voltages which include a common term that is related to the distance between the transmitter and the receiver as well as a differential term that is proportional to the volume flow intersecting the acoustic wave beam. By subtracting the two values, the common term related to distance is eliminated, leaving only the differential value which corresponds to the volume flow in the vessel. The present system is operated through one cycle each 500 $\mu$sec so that it completes two cycles or a complete measurement every millisecond, thereby producing a continuous output signal which is indicative of the varying volume flow in the conduit 24.

The theory of operation by which it can be shown that, in general, a transit time signal which is acquired to evenly represent the full flow through an area carries a measure of the volume flow through such area, and more specifically, the fact that the output from subtractor 100 in FIG. 6 is proportional to the volume flow in conduit 24 may be explained as follows, with reference being made to FIG. 1 for definitions of the coordinate system and dimensions. Considering an arrangement as depicted in FIG. 1 wherein part of a rectangular beam of radiation intersects a moving fluid, a Cartesian coordinate system is chosen with the x-axis along the beam, and with the y and z axes aligned with the lateral dimensions of the beam. A narrow ray within this beam requires a time T to travel the distance L between the transducers 14 and 16 which define the start and finish reference planes for the beam. This transit time T for an infinitesimal beam may be expressed as follows:

$$T(x,y,z) = \int_0^L \frac{dx}{c \pm v_x(x,y,z)} \quad \text{(Equation 1)}$$

where c is the propogating velocity of the ray in a stationary medium, and thus is equal to the velocity of sound when the beam is an acoustic wave, $v_x(x,y,z)$ is the vector component of the velocity of the moving fluid along the axis of the ray, and where the plus or minus sing ($\pm$) denotes the two opposing directions of travel of the beam between the two reference planes (i.e., the upstream and the downstream measurements).

The velocity of the fluid to be measured is generally much less than the velocity of the beam ($v << c$). A truncated series expansion of the denominator in equation 1 then yields:

$$T(x,y,z) = \frac{L}{c} \pm T(v) \quad \text{(Equation 2)}$$

$$T(v) = \frac{1}{c^2} \int_0^L v_x(x,y,z)dx$$

If it is assumed that the transmitted signal leaving one of the reference pleans 14 or 16 is uniform in intensity and spectral content across the rectangular area of illumination, and more specifically in the z-direction of the beam as illustrated in FIG. 1, every infinitesimal ray will arrive at the opposing reference plane as a time-delayed version of the transmitted signal, with an amplitude proportional to the ray thickness (dydz) and to the signal coupling between the two reference planes, $G_{tr}$. In the preferred embodiment, $G_{tr}$ accounts for factors such as beam geometry, transducer alignment, and medium attenuation. The full received signal at the receiving plane is found by integrating these constituents across the beam area $S_b$:

$$f_r = \iint_{S_b} G_{tr} \cdot f_t[t - \frac{L}{c} \pm T(v)] \cdot dydz \quad \text{(Equation 3)}$$

where $f_r$ is the received signal and the term $f_t[t-(L/c)\pm T(v)]$ is the time delayed function of the acoustic beam. It is assumed that $G_{tr}$ is constant across the full beam width. A Taylor-expansion of the time delayed function $f_5$ around the term $t-(L/c)$ yields:

$$f_t[t - \frac{L}{c} \pm T(v)] = f_t(t - \frac{L}{c}) \pm T(v) f_t'(t - \frac{L}{c}) + R \quad \text{(Equation 4)}$$

where:

$$R = \frac{[T(v)^2 f_t''(t - \frac{L}{c})]}{2}! + \text{higher order terms.}$$

The foregoing series expansion represents the original function when $F_t$ has continuous derivatives around $[t-(L/c)]$ and the higher order terms approach zero. The transmitted signal is chosen so that the higher order terms contained in the function R can be neglected, and this occurs when the transit time deviation induced by the velocity of the fluid medium is small compared to the wave length of the highest frequency present in the transmitted signal. In such a case, the received signal $f_r$ is then described as follows:

$$f_r = G_{tr}f_t(t - \frac{L}{c})S_b \pm G_{tr}f_t'(t - \frac{L}{c}) \iint_{S_b} T(v)dydz \quad \text{(Equation 5)}$$

T(v) is zero for those parts of the beam which do not intersect the fluid-carrying vessel, so the integral over the beam area $S_b$ need only be calculated over the area $S_v$ which actually intersects the vessel, and for that area:

$$\iint_{S_b} T(v)dydz = \int_{S_v} \frac{1}{c^2} \int_0^L v_x(x,y,z) dxdydz \quad \text{(Equation 6)}$$

$$= \frac{1}{c^2} \iiint_{V_{vb}} v_x(x,y,z) dxdydz$$

where $V_{vb}$ is the intersecting volume of the vessel and the beam. The integral represented by equation 6 provides the volume flow rate in the x direction ($Q_x$) multiplied by the length of the vessel $w_y$ over wich $Q_x$ is averaged. With w being equal to the width of a beam, and $\phi$ being the angle between the axis of flow through the vessel and the beam axis, the term $w_y = w \cos \phi$. Thus, for an axial flow through the vessel, where $Q_a$ is the component of volume flow along the axis of the vessel: $Q_a = Q_x/\sin \phi$, and equation 6 simplifies into the following:

$$\iint_{S_b} T(v)dydz = \frac{1}{c^2} w \tan\phi \cdot Q_a \quad \text{(Equation 7)}$$

The foregoing yields for the received signal:

$$f_r = G_{tr}f_t(t - \frac{L}{c})S_b \pm G_{tr}f_t'(t - \frac{L}{c}) \frac{w \tan\phi \, Q_a}{c^2} \quad \text{(Equation 8)}$$

In a typical interferometric system, where upstream and downstream measurements are taken, the readings are subtracted to eliminate the portions of the signal representing zero flow signal transmission, leaving:

$$\Delta f_r = 2 G_{tr}f_t'(t - \frac{L}{c}) \frac{w \tan\phi \, Q_a}{c^2} \quad \text{(Equation 9)}$$

so that it is possible to acquire a transit time differential signal which is proportional to the volume rate of flow through the measuring wave beam.

Since the described system is sensitive to the difference between the attenuation produced by the flowing medium and its surrounding medium, it is important to match the two for homogenous signal transmission, or to select an operating frequency where such differences are negligible. With the wave beam discussed so far, the component of volume flow along the beam is measured. However, when non-axial components are present in the flow (secondary flow, turbulence etc.) the relation between the measured flow and the actual volume of fluid transported axially will generally be unknown. In such cases, the volume flow can be measured by utilizing a reflectable radiation beam such as light or ultrasound and causing the beam to intersect the flow path more than once, as shown in FIG. 3, in order to eliminate the radial component of the flow vector.

The foregoing derivation is presented for the special case of a rectangular beam of radiation of constant intensity, and the invention has been discussed in terms of constrained flow due to the physical presence of a conduit. However, the volume of an unrestrained but spacially limited flow, such as a jet stream, can equally be measured with the method and apparatus of the present invention. Further, the wave beam need not be rectangular, but may have arbitrary boundaries and intensity distribution, as long as the transmitter to receiver coupling $G_{tr}$ is constant across the full cross-sectional area of flow. This may be accomplished by appropriate selection of the received signal and compensations for intensity variations. Thus, for example, if a light wave beam of arbitrary geometry is selected for use in measuring a volume flow, the beam may be formed, through suitable beamsplitters and mirrors, to travel two paths and to intersect the fluid flow simultaneously at spaced upstream and downstream locations, the two beams thereafter intersecting and thus interfering at a selected location. An optical sensing array may be positioned at the location of the interference, and may be so arranged as to receive only a selected rectangular area of the interference pattern, thereby limiting the dimensions of the measured flow. Compensation for variations in the intensity of the illuminating beam can be obtained by varying the sensitivity of corresponding parts of the receiving array. Similar constraints may be placed on other radiating beams and on the receiving sensors.

In the preferred embodiment of the present invention, the radiation consists of bursts of an acoustic wave beam, the wave being a single frequency in the ultrasonic range. In this case, and assuming a unit-strength transmitter signal where $f_t = \sin \omega t$, the received signal may be expressed:

$$f_r = G_{tr}S_b \sin\omega(t - \frac{L}{c}) \pm Q_a \frac{G_{tr}w\,\omega\,\tan\phi}{c^2} \cos\omega(t - \frac{L}{c}) \quad \text{(Equation 10)}$$

From the foregoing expression, it is found that the received signal contains an AC term the amplitude of which is proportional to the volume flow through the vessel. Furthermore, the sign change of this term when the direction of the sound beam is reversed produces an accurate means of establishing the zero flow reference, as explained above.

The sum of the two terms expressed in equation 10 can alternately be expressed as a product:

$$f_r = G_{tr}S_{tr}\sqrt{1 + (\frac{\tan\phi Q_a}{c^2h})^2} \cdot \sin(\omega t - \omega\frac{L}{c} \pm \text{Arctan}\frac{\omega \tan\phi Q_a}{c^2h}) \quad \text{(Equation 11)}$$

from which it may be seen that the received signal is both amplitude and phase modulated by the intersecting volume flow, and either modulation may be detected.

In the embodiment illustrated in FIG. 6, it is the phase modulation which is detected. In this case, the unit is operated at a frequency at which the flow-induced phase shift in the wave beam is only a couple of degrees, and the arctangent function in Equation 11 can, therefore, be approximated by its argument.

In the receiver amplifier stage 70 of FIG. 6, the signal of Equation 11 is multiplied and clipped to a square wave, to produce a voltage U at line 72:

$$U_{72} = \sum_n \frac{1}{n} \sin\left\{n\omega(t - \frac{L}{c} \pm \frac{\tan\phi\, Q_a}{c^2h})\right\} \text{for } n = 1,3,5,7\ldots \quad \text{(Equation 12)}$$

The synchronous detector 74 determines the L.F. component of the product of the foregoing expression and the square wave analogon of the instantaneous H.F. oscillator signal:

$$U_{80} = L.F. \text{ of } \{U_{72} \cdot \sum_n \frac{1}{n} \sin(n\omega t)\} \quad \text{(Equation 13)}$$

$$= \frac{1}{2} \sum_n \frac{1}{n^2} \cos\{n\omega(\frac{L}{c} \pm \frac{\tan Q_a}{c^2h})\}$$

$$= \frac{1}{2} \sum_n \frac{1}{n^2} \cos(n\omega \frac{L}{c})\cos(n\omega \frac{\tan\phi Q_a}{c^2h}) \pm$$

$$\sum_n \frac{1}{n} \sin(n\omega \frac{L}{c})\sin(n\omega \frac{\tan\phi Q_a}{c^2h})$$

The first term in this expression is a distance related phase shift common to both the upstream and the downstream measurement, while flow information is contained in the second, differential term.

The integrate and hold module 82 resets before an average phase reading is made, and then produces an average phase reading by integrating over a fixed period of time. Each reading is used to update one or the other of the respective sample and hold modules 96 and 98. The subtractor 100 then eliminates the common mode term in equation 13:

$$U_{106} = \sum_n \frac{1}{n^2} \sin(n\omega \frac{L}{c}) \sin(n\omega \frac{\tan\phi Q_a}{c^2h}) \quad \text{(Equation 14)}$$

Where the flow-induced phaseshifts are relatively small, the Sinus of the flowterm can be approximated by the flowterm itself, yielding for the output signal at line 106:

$$U_{106} = \frac{\omega \tan\phi}{c^2h} Q_a \sum_n \frac{1}{n} \sin(n\omega \frac{L}{c}) \quad n = 1,3,5,\ldots \quad \text{(Equation 15)}$$

This output signal is thus directly proportional to the volume flow $Q_a$ intersecting the beam of ultrasound. The proportionality constant is frequency- and geometry-dependent, and needs to be determined by a precalibration of a specific probe, as is commonly done. The sum of Sinusses in equation 15 is the series expansion of a square wave, equal to either $+1$ or $-1$ depending upon the zero flow distance between transmitter and receiver in number of wavelengths. Frequencies where this term changes sign have to be avoided, as readout errors may result.

Thus, there has been disclosed a new and unique volume flow measurement device which utilizes ultrasonic waves to traverse the flowing fluid and to produce electric signals representing the time delays imposed on those waves by moving fluid. The measurement of the fluid is done in an upstream and a downstream direction to eliminate nonflow parameters from the resulting signals and to produce a differential component which represents the volume of the fluid passing through the acoustic beam. This device eliminates the need for measuring the inside diameter of the vessel carrying the fluid, and produces a signal which is to a high degree independent of flow profile, vessel geometry, and alignment of the vessel within the probe beam.

Although the invention has been illustrated in terms of a preferred embodiment, it will be understood that numerous variations and modifications can be made by those of skill in the art without departing from the true spirit and scope of the inventive concept as set forth in the following claims.

I claim:

1. A flow measurement device for obtaining a signal representive of the volume flow of a fluid, comprising:
    a first transducer for producing and for receiving acoustic waves capable of being modified by the flow of a fluid;
    a second transducer for producing and for receiving acoustic waves capable of being modified by the flow of said fluid;
    means for positioning said first and second transducers to illuminate substantially uniformly the entire diameter of said fluid flow by waves produced by said transducers, said transducers being so related that the fluid to be measured will have a component of flow along the axis of said waves;
    first means for energizing said first transducer to produce a first beam of said waves for a first period of time in a first direction with respect to said component of flow; said wave beam being directed to and received by said second transducer to produce first electrical signals representing the received waves;
    second means for energizing said second transducer to produce a second beam of said waves for a second period of time in a second direction with respect to said component of flow, said second wave beam being directed to and received by said first transducer to produce second electrical signals representing the received waves;
    said first and second means for energizing said first and second transducers comprising oscillator means producing a high frequency electrical output, normally deactivated first and second gate means connecting said oscillator output to said first and second transducers, respectively, and control means for periodically and alternately activating said first and second gate means in transmit modes to produce bursts of acoustic waves which travel between said first and second transducers;
    receiver means responsive to said first and second electrical signals produced by said second and first transducers, respectively, said receiver means being connected to said first and second transducers by said first and second gate means, respectively, said control means periodically and alternately activating said gate means in receive modes to permit said first and second electrical signals to travel to said receiver means;
    synchronous detector means connected to said receiver means and to said oscillator means for alternately comparing each of said first and second electrical signals with the high frequency output of said oscillator to produce corresponding alternate first and second variable signals;
    integrator means for alternately integrating each of said first and second variable signals to produce first and second output signals corresponding to said first and second electrical signals; and
    means responsive to the difference between said first and second output signals for producing a resultant signal which is proportional to the volume flow of said fluid.

2. The flow measuring device of claim 1, wherein said means responsive to the difference between said first and second output signals comprises:
    a first sample and hold circuit for sampling and storing a valve corresponding to said first output signal;
    a second sample and hold circuit for sampling and storing a second value corresponding to said second output signal; and
    means for comparing said first and second values, for providing said resultant signal corresponding to the volume flow signal.

3. The flow measuring device of claim 1, wherein said integrator means is a normally deactivated gated integrator, and wherein said control means operates in its receive modes to activate said gated integrator and a selected one of said sample and hold circuits.

4. The flow measuring device of claim 3, wherein said oscillator means includes a normally deactivated gated power amplifier for supplying said high frequency electrical output to said first and second gate means, said control means activating said gated power amplifier only in said transmit mode.

5. The flow measuring device of claim 1, further including housing means defining a cavity and means for mounting said first and second transducers in said housing so that said waves produced by said transducers illuminate the entire cross section of said cavity with a substantially constant wave intensity, said cavity being adapted to receive said fluid flow.

6. The flow measuring device of claim 5, wherein said fluid flows through a conduit, and wherein said cavity is adapted to receive said conduit.

7. The flow measuring device of claim 6, wherein said fluid is blood, and said conduit is a blood vessel, said resultant signal being proportional to the volume flow of said blood and independent of flow profile or vessel wall thickness.

8. The flow measuring device of claim 7, wherein said conduit is of a material which has a wave attenuation comparable to that of said fluid.

9. The volume flow measurement device of claim 1, wherein said first and second transducers are located on diametrically opposed sides of the flow path of said fluid.

10. The volume flow measurement device of claim 1, wherein said first and second transducers are located on the same side of the flow path of said fluid, said device further including a wave reflective surface aligned with the waves transmitted by said transducers and located on the side of said flow path diametrically opposed to the location of said transducers, said transducers and said reflective surface being angularly related so that the beam of waves produced by one transducer will be received by the other transducer after reflection from said reflective surface, whereby the beam of waves will pass twice through said fluid flow path.

11. A flow measurement system for obtaining a resultant signal representative of the volume flow of a fluid stream, comprising:
    first and second acoustic wave transducers adapted to be located adjacent the fluid stream, said transducers being so located that an acoustic wave beam transmitted by one transducer will pass through said fluid stream and will impinge on the other transducer;
    means for generating a drive signal for activating said transducers, said drive signal being of an amplitude and frequency sufficient to drive said transducers to produce ultrasonic wave beams, said transducers each producing a wave beam of sufficient dimension to illuminate with uniform intensity tne entire cross section of the portion of the fluid stream to be measured;

control means for periodically and alternately switching said transducers between transmit and a receive modes, whereby said drive signal is applied to said first transducer and the resulting acoustic wave beam is received by said second transducer and thereafter said drive signal is applied to said second transducer and the resulting acoustic wave beam is received by said first transducer;

synchronous detector means for comparing the signal received by said second transducer with said drive signal to provide a first variable signal and for comparing the signal received by said first transducer with said drive signal to provide a second variable signal;

means for integrating each of said first and second variable signals to produce first and second output signals; and means responsive to the difference between said first and second output signals for producing a resultant signal which is proportional to the volume flow of said fluid stream.

12. The flow measurement system of claim 11, wherein said transducers are so located with respect to said fluid stream that said wave beam transmitted by said first transducer passes through said fluid at an upstream angle, and said wave beam transmitted by said second transducer passes through said fluid at a downstream angle, and wherein said first output signal is proportional to the transit time of said first beam and said second output signal is proportional to the transit time of said second beam, said resultant signal being proportional to the difference in transit times, and this proportional to fluid volume flow.

13. The flow measurement system of claim 11, wherein said means responsive to the difference between said first and second output signals includes first and second sample and hold circuits.

* * * * *